US010602776B2

(12) United States Patent
Batista

(10) Patent No.: US 10,602,776 B2
(45) Date of Patent: Mar. 31, 2020

(54) AEROSOL-FORMING CARTRIDGE WITH PROTECTIVE FOIL

(71) Applicant: PHILIP MORRIS PRODUCTS S.A., Neuchatel (CH)

(72) Inventor: Rui Nuno Batista, Morges (CH)

(73) Assignee: PHILIP MORRIS PRODUCTS S.A., Neuchatel (CH)

(*) Notice: Subject to any disclaimer, the term of this patent is extended or adjusted under 35 U.S.C. 154(b) by 595 days.

(21) Appl. No.: 15/323,908

(22) PCT Filed: Jul. 9, 2015

(86) PCT No.: PCT/EP2015/065768
§ 371 (c)(1),
(2) Date: Jan. 4, 2017

(87) PCT Pub. No.: WO2016/005531
PCT Pub. Date: Jan. 14, 2016

(65) Prior Publication Data
US 2017/0144827 A1  May 25, 2017

(30) Foreign Application Priority Data
Jul. 11, 2014  (EP) .................... 14176830

(51) Int. Cl.
*A24F 47/00* (2020.01)
*A61M 15/06* (2006.01)
(Continued)

(52) U.S. Cl.
CPC .......... *A24F 47/008* (2013.01); *A24B 15/167* (2016.11); *A61M 15/06* (2013.01);
(Continued)

(58) Field of Classification Search
CPC .................................................. A24F 47/008
See application file for complete search history.

(56) References Cited

U.S. PATENT DOCUMENTS

| 5,224,498 A | 7/1993 | Deevi et al. |
| 5,388,594 A | 2/1995 | Counts et al. |

(Continued)

FOREIGN PATENT DOCUMENTS

| CN | 2285659 Y | 7/1998 |
| CN | 102379458 A | 3/2012 |

(Continued)

OTHER PUBLICATIONS

Combined Office Action and Search Report dated Feb. 22, 2019 in Chinese Patent Application No. 201580032357.0, 14 pages (with English translation).

(Continued)

*Primary Examiner* — Anthony Calandra
(74) *Attorney, Agent, or Firm* — Oblon, McClelland, Maier & Neustadt, L.L.P.

(57) ABSTRACT

There is provided an aerosol-forming cartridge for an electrically operated aerosol-generating system. The aerosol-forming cartridge includes a base layer including at least one cavity and at least one aerosol-forming substrate held in the at least one cavity. A protective foil is removably attached to the base layer and is arranged to substantially hermetically seal the at least one aerosol-forming substrate within the at least one cavity prior to use of the aerosol-forming cartridge.

14 Claims, 6 Drawing Sheets

(51) Int. Cl.
  *A24B 15/16*   (2020.01)
  *A24B 15/167*  (2020.01)
  *B65D 17/50*   (2006.01)
  *B65D 25/04*   (2006.01)
  *B65D 85/00*   (2006.01)

(52) U.S. Cl.
  CPC ........... *B65D 17/501* (2013.01); *B65D 25/04* (2013.01); *B65D 85/54* (2013.01)

(56) References Cited

U.S. PATENT DOCUMENTS

| | | | |
|---|---|---|---|
| 5,408,574 A | | 4/1995 | Deevi et al. |
| 5,505,214 A | | 4/1996 | Collins et al. |
| 5,591,368 A | | 1/1997 | Fleischhauer et al. |
| 6,098,632 A | * | 8/2000 | Turner .................. A24F 47/002 131/270 |
| 2009/0078671 A1 | * | 3/2009 | Triquet .................. B65D 51/20 215/232 |
| 2010/0101590 A1 | * | 4/2010 | Pflaum ..................... A24D 1/14 131/222 |
| 2012/0132204 A1 | | 5/2012 | Lucking et al. |
| 2013/0042864 A1 | | 2/2013 | Adler et al. |
| 2013/0146489 A1 | | 6/2013 | Scatterday |
| 2014/0060554 A1 | | 3/2014 | Collett et al. |
| 2014/0069829 A1 | * | 3/2014 | Evans ..................... A24F 23/02 206/265 |
| 2015/0027459 A1 | | 1/2015 | Collett et al. |
| 2017/0095624 A1 | * | 4/2017 | Davidson ............ A61M 15/005 |

FOREIGN PATENT DOCUMENTS

| | | |
|---|---|---|
| CN | 103068266 A | 4/2013 |
| EP | 0 857 431 A1 | 8/1998 |
| EP | 1 736 062 A2 | 12/2006 |
| EP | 2 316 286 A1 | 5/2011 |
| JP | 4-259471 A | 9/1992 |
| JP | 2003-509142 A | 3/2003 |
| JP | 2010-516319 A | 5/2010 |
| JP | 2014-37794 A | 2/2014 |
| WO | WO 01/83326 A1 | 11/2001 |
| WO | WO 2004/041007 A2 | 5/2004 |
| WO | WO 2005/014437 A2 | 2/2005 |
| WO | WO 2007/024130 A1 | 3/2007 |
| WO | WO 2007/066374 A1 | 6/2007 |
| WO | WO 2007/131449 A1 | 11/2007 |
| WO | WO 2007/131450 A1 | 11/2007 |
| WO | WO 2014/037794 A2 | 3/2014 |

OTHER PUBLICATIONS

International Search Report and Written Opinion of the International Searching Authority dated Sep. 28, 2015 in PCT/EP2015/065768 filed Jul. 9, 2015.

Japanese Office Action dated Jul. 25, 2019 in Japanese Patent Application No. 2017-501376 (with English translation), 10 pages.

* cited by examiner

AEROSOL-FORMING CARTRIDGE WITH PROTECTIVE FOIL

The present disclosure relates to an aerosol-forming cartridge for use in an electrically operated aerosol-generating system. In particular, the present invention relates to aerosol-forming cartridges having a base layer with at least one cavity and having at least one aerosol-forming substrate held in the at least one cavity.

One type of aerosol-generating system is an electrically operated smoking system. Handheld electrically operated smoking systems consisting of an electric vaporiser, an aerosol-generating device comprising a battery and control electronics, and an aerosol-forming cartridge are known. The vaporiser is typically an electric heater, although other types of vaporiser, such as an ultrasonic device or a piezo-electric device are known. Typically, aerosol-forming cartridges for use with aerosol-generating devices comprise an aerosol-forming substrate that is assembled, often with other elements or components, in the form of a rod. For example, WO-A-2004/041007 describes an aerosol-generating system comprising a rod-shaped, electrically heated cartridge and an aerosol-generating device having a cylindrical cavity for receiving the cartridge. The cartridge comprises a tobacco rod containing volatile tobacco flavour compounds that are releasable when heated by the device. Typically, a number of such cartridges is packaged together in a pack, which is generally overwrapped with a clear film to protect the aerosol-forming cartridges during transport and storage. However, such overwrapping increases the cost for packaging multiple cartridges together and, once a pack has been opened, the individual cartridges may begin to lose volatile compounds, reducing their effectiveness. This may lead to an unacceptable variance in the quality of aerosol produced by different cartridges in the pack.

To overcome this, it is known to wrap cartridges together in smaller bundles, for example as described in WO-A-2005/014437, or to individually wrap each cartridge, for example as described in WO-A-01/83326. However, such packs may be expensive to produce, due to the material required and the complex assembly required, and may be difficult for a user to handle when opening.

According to a first aspect of the present invention, there is provided an aerosol-forming cartridge for use in an electrically heated aerosol-generating system, the aerosol-forming cartridge comprising: a base layer comprising at least one cavity; at least one aerosol-forming substrate held in the at least one cavity; and a protective foil removably attached to the base layer and arranged to substantially hermetically seal the at least one aerosol-forming substrate within the at least one cavity prior to use, wherein the base layer and the at least one aerosol-forming substrate are in contact at a substantially planar first contact surface and the base layer and the protective foil are in contact at a substantially planar second contact surface, and wherein the first and second contact surfaces are substantially parallel.

Providing the cartridge with a protective foil to hermetically seal the aerosol-forming substrate within the cavity prior to use ensures that the cartridge remains fresh after a pack containing the aerosol-forming cartridge has been opened. When the cartridge is required by a user, the protective foil is removed from the base layer to break the seal and expose the aerosol-forming substrate. Thus, the quality of aerosol produced by each cartridge does not depend on the delay between opening the pack and consuming each cartridge. This can reduce the variance in the quality of aerosol produced by different cartridges in the pack Further, it also removes the requirement to overwrap the pack itself, reducing the cost for packaging multiple cartridges together. Holding the at least one aerosol-forming substrate in the at least one cavity helps to maintain correct positioning of the aerosol-forming substrate within the cartridge and makes it easier to seal the aerosol-forming substrate within the cartridge.

In addition, by having substantially planar and parallel contact surfaces, the cartridge can be advantageously manufactured using only vertical assembly operations. This simplifies the manufacture of the cartridge by removing the need for more complex assembly operations, such as rotational or multi-translational movements of the cartridge or its components, as known in the manufacture of cylindrical objects, such as cigarettes. Such cartridges can also be made using fewer components than conventional cartridges and are generally more robust. The protective foil can also be more easily removed by a user.

As used herein, the term "cartridge" refers to a consumable article which is configured to couple to and uncouple from an aerosol-generating device to form an aerosol-generating system and which is assembled as a single unit that can be coupled and uncoupled from the aerosol-generating device by a user as one when the article has been consumed.

As used herein, the term "aerosol-forming cartridge" refers to a cartridge comprising an aerosol-forming substrate that is capable of releasing volatile compounds that can form an aerosol. For example, an aerosol-generating cartridge may be a smoking article.

As used herein, the term "protective foil" refers to a thin sheet of substantially gas impermeable material.

As used herein, the term "hermetically seal" means that the weight of volatile compounds in the aerosol-forming substrate changes by less than 2 percent over a two week period, preferably over a two month period, more preferably over a two year period.

As used herein, the term "contact" includes direct contact between two components of the cartridge, as well as indirect contact via one or more intermediate components of the cartridge, such as coatings or laminated layers. As used herein, the term "substantially planar", means arranged substantially along a single plane.

Preferably, the cartridge further comprises a cover layer fixed to the base layer and over the aerosol-forming substrate to retain the at least one aerosol-forming substrate in the at least one cavity, the cover layer comprising at least one gas permeable window.

With this arrangement, the aerosol-forming substrate is held in the at least one cavity by the cover layer after the protective foil has been removed. This makes it easier to couple the cartridge to an aerosol-generating device. In use, aerosol released by the aerosol-forming substrate passes through the at least one gas permeable window.

The cover layer may be fixed to the base layer by virtue of being formed integrally with the base layer. Alternatively, the cover layer may be a separate component fixed directly to the base layer, or indirectly via one or more intermediate layers or components.

The at least one gas permeable window may be a single gas permeable window. Alternatively, the at least one gas permeable window may comprise a plurality of gas permeable windows. In certain embodiments, the base layer comprises a plurality of cavities and each of the plurality of gas permeable windows is associated with one or more of the plurality of cavities.

The at least one gas permeable window may comprise one or more apertures. Alternatively, at least one gas permeable window may comprise one or more perforated membranes or grids extending across one or more apertures in the cover layer. The grid may be of any suitable form, such as a transverse grid, longitudinal grid, or mesh grid. The cover layer may form a seal with the base layer. The cover layer may form a hermetic seal with the base layer. The cover layer may comprise a polymeric coating at least where the cover layer is fixed to the base layer, the polymeric coating forming a seal between the cover layer and the base layer.

Preferably, the protective foil is substantially planar and is arranged to substantially hermetically seal the aerosol-forming substrate within the at least one cavity by closing the at least gas permeable window. In such embodiments, the cover layer preferably forms a hermetic seal with the base layer.

With this arrangement, the amount of protective foil required is less, since it only needs to be large enough to cover the at least one gas permeable window. This arrangement can also simplify and reduce the cost for cartridge manufacture, since the protective foil does not need to be wrapped around any of the components of the cartridge but simply placed over the window. It also means that the protective foil can be removed by pulling it in a single direction, improving the ease with which the protective foil can be removed by a user.

Preferably, the area of the at least one gas permeable window is less than the area of the at least one cavity and the remainder of the cover layer is substantially gas impermeable.

Preferably, one or more of the base layer, the protective foil and the at least one aerosol-forming substrate is substantially flat. As used herein, the term "substantially flat" means having a thickness to width ratio of at least 1:2, preferably from 1:2 to about 1:20. This includes, but is not limited to having a substantially planar shape. Flat components can be easily handled during manufacture and provide for a robust construction. In addition, it has been found that aerosol release from the aerosol-forming substrate is improved when it is substantially flat and when a flow of air is drawn across the width, length, or both, of the aerosol-forming substrate.

In certain embodiments, one or more of the base layer, the protective foil and the at least one aerosol-forming substrate has a non-curved cross-section. This reduces the amount of rolling movement during manufacture, improving assembly precision and ease of assembly. In certain embodiments, one or more of the base layer, the protective foil and the at least one aerosol-forming substrate is substantially planar.

The protective foil may be removable attached to the base layer by any suitable method, for example by thermal bonding, welding, using adhesive, or any combination thereof.

In certain preferred embodiments, the protective foil is removably attached to the base layer by ultrasonic welding along a continuous sealing line. Where the cartridge further comprises a cover layer fixed to the base layer and over the aerosol-forming substrate and comprising a gas permeable window, the continuous sealing line preferably extends around the periphery of the at least one gas permeable window. Where the cover layer comprises more than one gas permeable window, the protective foil may be removably attached to the cover layer along more than one continuous sealing line. The continuous sealing line may be formed from a single weld line. Alternatively, the continuous sealing line may be formed from two or more weld lines. In certain preferred embodiments, the continuous sealing line comprises first and second continuous weld lines arranged side by side. The first and second weld lines provide a double seal. With this arrangement, if one of the first or second continuous weld lines is damaged or incomplete, the seal will remain intact due to the other of the first or second continuous weld lines. In certain preferred embodiments, the continuous sealing line comprises one or more weld lines each having a thickness of from about 300 μm to about 2000 μm.

Alternatively, or in addition, the protective foil may be removably attached to the base layer using an adhesive.

The protective foil may be formed from any suitable material. Preferably, the protective foil is formed from a flexible film, such as a flexible film comprising a polymer film, a metallised film, a metallised paper film, a laminated metal foil, or any combination thereof. The protective foil may comprise a polymeric foil. The polymeric foil may comprise any suitable material, such as, but not limited to, one or more of a Polyimide (PI), a Polyaryletherketone (PAEK), such as Polyether Ether Ketone (PEEK), Poly Ether Ketone (PEK), or Polyetherketoneetherketoneketone (PEKEKK), or a Fluoric polymer, such as Polytetrafluoroethylene (PTFE), Polyvinylidene Fluoride (PVDF), Ethylene tetrafluoroethylene (ETFE), PVDFELS, or Fluorinated Ethylene Propylene (FEP). The protective foil may comprise a multilayer polymeric foil.

The protective foil may have one or more free ends at which a tab is provided to allow a user to easily grasp and remove the protective foil. The tab may be formed by an extension of the protective foil. The tab may extend beyond the edge of the cartridge. In preferred embodiments, the tab may comprise a grip portion having an increased friction coefficient.

The protective foil may comprise a first portion that is removably attached to the base layer and a second portion that is attached to the first portion, the second portion extending from the first portion to form a tab by which a user can remove the first portion from the base layer. The protective foil may be arranged on the cover layer as a single planar sheet. In certain preferred embodiments, the protective foil is folded over itself at a fold line between the first and second portions such that that the first and second portions are substantially co-planar.

With this arrangement, the protective foil can be easily removed by pulling the tab longitudinally to peel the first portion away from the cover layer at the fold line. That is, the protective foil can be removed by pulling the tab in a direction having a component which is parallel to the plane of the protective foil and substantially perpendicular to the fold line.

The at least one aerosol-forming substrate may comprise a single aerosol-forming substrate. Alternatively, the at least one aerosol-forming substrate may comprise a plurality of aerosol-forming substrates. The plurality of aerosol-forming substrates may have the substantially the same composition. Alternatively, the plurality of aerosol-forming substrates may comprise two or more aerosol-forming substrates having substantially different compositions. The plurality of aerosol-forming substrates may be stored together on the base layer. Alternatively, the plurality of aerosol-forming substrates may be stored separately. In certain preferred embodiments, the at least one aerosol-forming substrate comprises first and second aerosol-forming substrates and the base layer comprises first and second cavities in which the first and second aerosol-forming substrates are stored separately.

By separately storing two or more aerosol-forming substrates, it is possible to store two substances which are not entirely compatible in the same cartridge. Advantageously, separately storing two or more aerosol-forming substrates may extend the life of the cartridge. It also enables two incompatible substances to be stored in the same cartridge. Further, it enables the aerosol-forming substrates to be aerosolised separately, for example by heating each aerosol-forming substrate separately. Thus, aerosol-forming substrates with different heating profile requirements can be heated differently for improved aerosol formation. It may also enable more efficient energy use, since more volatile substances can be heated separately from less volatile substances and to a lesser degree. Separate aerosol-forming substrates can also be aerosolised in a predefined sequence, for example by heating a different one of the plurality of aerosol-forming substrates for each use, ensuring a 'fresh' aerosol-forming substrate is aerosolised each time the cartridge is used. In certain embodiments, one or more of the aerosol-forming substrates may be heated to release aerosol, while one or more of the other aerosol-forming substrates may be sufficiently volatile that aerosol is released without the need for heating.

Where the at least one aerosol-forming substrate comprises a plurality of aerosol-forming substrates and the base layer comprises a plurality of cavities in which the plurality of aerosol-forming substrates are held, the protective foil may be arranged for removal in stages to selectively open one or more of the cavities independently for one or more of the other cavities. Advantageously, this allows the user to vary the concentration, composition, or concentration and composition of the aerosol released by the cartridge by removing the protective foil to a lesser or greater extent.

In certain embodiments, the at least one aerosol-forming substrate comprises first and second aerosol-forming substrates and the base layer comprises first and second cavities in which the first and second aerosol-forming substrates are stored separately, and the protective foil is arranged for removal in stages to selectively open the first and second cavities independently. For example, the protective foil may comprise one or more removable sections, each of which is arranged to reveal one or more of the cavities when removed from the remainder of the protective foil. Alternatively, or in addition, the protective foil may be attached to the base layer such that the required removal force varies between the various stages of removal as an indication to the user. For example, the required removal force may increase between adjacent stages so that the user must deliberately pull harder on the protective foil to continue removing the protective foil to reveal further cavities. This may be achieved by any suitable means. For example, the required removal force may be varied by altering the type, quantity, or shape of an adhesive layer, or by altering the shape or amount of a weld line by which the protective foil is attached. Alternatively, or in addition, the protective foil may include one or more indication marks to inform a user of the extent to which the protective foil has been removed.

The force required to detach the protective foil from the cartridge is preferably from about 1 N to about 10 N, more preferably from about 3 N to about 8 N, and most preferably about 5 N. The cartridge may further comprise one or more frangible capsules between the protective foil and the base layer which contain one or more flavour compounds, fragrance compounds, or flavour and fragrance compounds, and which are broken when the protective foil is removed or partially removed from the base layer. In certain preferred embodiments, the frangible capsules may contain menthol.

In any of the embodiments described above, the at least one aerosol-forming substrate may comprise nicotine. For example, the at least one aerosol-forming substrate may comprise a tobacco-containing material with volatile tobacco flavour compounds which are released from the aerosol-forming substrate upon heating. Preferably, the at least one aerosol-forming substrate comprises an aerosol former, that is, a substance which generates an aerosol upon heating. The aerosol former may be, for instance, a polyol aerosol former or a non-polyol aerosol former. It may be a solid or liquid at room temperature, but preferably is a liquid at room temperature. Suitable polyols include sorbitol, glycerol, and glycols like propylene glycol or triethylene glycol. Suitable non-polyols include monohydric alcohols, such as menthol, high boiling point hydrocarbons, acids such as lactic acid, and esters such as diacetin, triacetin, triethyl citrate or isopropyl myristate. Aliphatic carboxylic acid esters such as methyl stearate, dimethyl dodecanedioate and dimethyl tetradecanedioate can also be used as aerosol formers. A combination of aerosol formers may be used, in equal or differing proportions. Polyethylene glycol and glycerol may be particularly preferred, whilst triacetin is more difficult to stabilise and may also need to be encapsulated in order to prevent its migration within the product. The at least one aerosol-forming substrate may include one or more flavouring agents, such as cocoa, liquorice, organic acids, or menthol. The at least one aerosol-forming substrate may comprise a solid substrate. The solid substrate may comprise, for example, one or more of: powder, granules, pellets, shreds, spaghettis, strips or sheets containing one or more of: herb leaf, tobacco leaf, fragments of tobacco ribs, reconstituted tobacco, homogenised tobacco, extruded tobacco and expanded tobacco. Optionally, the solid substrate may contain additional tobacco or non-tobacco volatile flavour compounds, to be released upon heating of the substrate. Optionally, the solid substrate may also contain capsules that, for example, include the additional tobacco or non-tobacco volatile flavour compounds. Such capsules may melt during heating of the solid aerosol-forming substrate. Alternatively, or in addition, such capsules may be crushed prior to, during, or after heating of the solid aerosol-forming substrate.

Where the at least one aerosol-forming substrate comprises a solid substrate comprising homogenised tobacco material, the homogenised tobacco material may be formed by agglomerating particulate tobacco. The homogenised tobacco material may be in the form of a sheet. The homogenised tobacco material may have an aerosol-former content of greater than 5 percent on a dry weight basis. The homogenised tobacco material may alternatively have an aerosol former content of between 5 percent and 30 percent by weight on a dry weight basis. Sheets of homogenised tobacco material may be formed by agglomerating particulate tobacco obtained by grinding or otherwise comminuting one or both of tobacco leaf lamina and tobacco leaf stems; alternatively, or in addition, sheets of homogenised tobacco material may comprise one or more of tobacco dust, tobacco fines and other particulate tobacco by-products formed during, for example, the treating, handling and shipping of tobacco. Sheets of homogenised tobacco material may comprise one or more intrinsic binders, that is tobacco endogenous binders, one or more extrinsic binders, that is tobacco exogenous binders, or a combination thereof to help agglomerate the particulate tobacco. Alternatively, or in addition, sheets of homogenised tobacco material may comprise other additives including, but not limited to, tobacco and non-tobacco fibres, aerosol-formers, humectants, plasticisers, flavourants, fillers, aqueous and non-aqueous solvents and combinations thereof. Sheets of homogenised tobacco material are preferably formed by a casting process of the type generally comprising casting a slurry comprising particulate tobacco and one or more binders onto a conveyor belt or other support surface, drying the cast slurry to form a sheet of homogenised tobacco material and removing the sheet of homogenised tobacco material from the support surface.

Optionally, the solid substrate may be provided on or embedded in a thermally stable carrier. The carrier may take the form of powder, granules, pellets, shreds, spaghettis, strips or sheets. Alternatively, the carrier may be a tubular carrier having a thin layer of the solid substrate deposited on its inner surface, such as those disclosed in U.S. Pat. Nos. 5,505,214, 5,591,368 and 5,388,594, or on its outer surface, or on both its inner and outer surfaces. Such a tubular carrier may be formed of, for example, a paper, or paper like material, a non-woven carbon fibre mat, a low mass open mesh metallic screen, or a perforated metallic foil or any other thermally stable polymer matrix. The solid substrate may be deposited on the surface of the carrier in the form of, for example, a sheet, foam, gel or slurry. The solid substrate may be deposited on the entire surface of the carrier, or alternatively, may be deposited in a pattern in order to provide a predetermined or non-uniform flavour delivery during use. Alternatively, the carrier may be a non-woven fabric or fibre bundle into which tobacco components have been incorporated, such as that described in EP-A-0 857 431. The non-woven fabric or fibre bundle may comprise, for example, carbon fibres, natural cellulose fibres, or cellulose derivative fibres.

As an alternative to a solid tobacco-based aerosol-forming substrate, the at least one aerosol-forming substrate may comprise a liquid substrate and the cartridge may comprise means for retaining the liquid substrate, such as one or more containers. Alternatively or in addition, the cartridge may comprise a porous carrier material, into which the liquid substrate is absorbed, as described in WO-A-2007/024130, WO-A-2007/066374, EP-A-1 736 062, WO-A-2007/131449 and WO-A-2007/131450.

The liquid substrate is preferably a nicotine source comprising one or more of nicotine, nicotine base, a nicotine salt, such as nicotine-HCl, nicotine-bitartrate, or nicotine-ditartrate, or a nicotine derivative.

The nicotine source may comprise natural nicotine or synthetic nicotine.

The nicotine source may comprise pure nicotine, a solution of nicotine in an aqueous or non-aqueous solvent or a liquid tobacco extract.

The nicotine source may further comprise an electrolyte forming compound. The electrolyte forming compound may be selected from the group consisting of alkali metal hydroxides, alkali metal oxides, alkali metal salts, alkaline earth metal oxides, alkaline earth metal hydroxides and combinations thereof.

For example, the nicotine source may comprise an electrolyte forming compound selected from the group consisting of potassium hydroxide, sodium hydroxide, lithium oxide, barium oxide, potassium chloride, sodium chloride, sodium carbonate, sodium citrate, ammonium sulfate and combinations thereof.

In certain embodiments, the nicotine source may comprise an aqueous solution of nicotine, nicotine base, a nicotine salt or a nicotine derivative and an electrolyte forming compound.

Alternatively or in addition, the nicotine source may further comprise other components including, but not limited to, natural flavours, artificial flavours and antioxidants.

In addition to a nicotine-containing aerosol-forming substrate, the aerosol-forming cartridge may further comprise a source of a volatile delivery enhancing compound that reacts with the nicotine in the gas phase to aid delivery of the nicotine to the user.

The volatile delivery enhancing compound may comprise a single compound. Alternatively, the volatile delivery enhancing compound may comprise two or more different compounds.

Preferably, the volatile delivery enhancing compound is a volatile liquid.

The volatile delivery enhancing compound may comprise an aqueous solution of one or more compounds. Alternatively the volatile delivery enhancing compound may comprise a non-aqueous solution of one or more compounds.

The volatile delivery enhancing compound may comprise two or more different volatile compounds. For example, the volatile delivery enhancing compound may comprise a mixture of two or more different volatile liquid compounds.

Alternatively, the volatile delivery enhancing compound may comprise one or more non-volatile compounds and one or more volatile compounds. For example, the volatile delivery enhancing compound may comprise a solution of one or more non-volatile compounds in a volatile solvent or a mixture of one or more non-volatile liquid compounds and one or more volatile liquid compounds.

In one embodiment, the volatile delivery enhancing compound comprises an acid. The volatile delivery enhancing compound may comprise an organic acid or an inorganic acid. Preferably, the volatile delivery enhancing compound comprises an organic acid, more preferably a carboxylic acid, most preferably an alpha-keto or 2-oxo acid.

In a preferred embodiment, the volatile delivery enhancing compound comprises an acid selected from the group consisting of 3-methyl-2-oxopentanoic acid, pyruvic acid, 2-oxopentanoic acid, 4-methyl-2-oxopentanoic acid, 3-methyl-2-oxobutanoic acid, 2-oxooctanoic acid and combinations thereof. In a particularly preferred embodiment, the volatile delivery enhancing compound comprises pyruvic acid.

As an alternative to a solid or liquid aerosol-forming substrate, the at least one aerosol-forming substrate may be any other sort of substrate, for example, a gas substrate, a gel substrate, or any combination of the various types of substrate described.

The term "base layer" refers to a layer of the cartridge which comprises at least one cavity in which the at least one aerosol-forming substrate is held. The term does not necessarily refer to the position of the layer within the cartridge. The base layer may be the lowermost layer of the cartridge, although it is not limited to this position.

The base layer may have any suitable cross-sectional shape. Preferably, the base layer has a non-circular cross-sectional shape. In certain preferred embodiments, the base layer has a substantially rectangular cross-sectional shape. In certain embodiments, the base layer has an elongate, substantially rectangular, parallelepiped shape. In certain preferred embodiments, the base layer is substantially flat.

The base layer may be formed from a single component. Alternatively, the base layer may comprise multiple layers or components which combine to form the base layer.

In any of the embodiments described above, the aerosol-forming cartridge may comprise a vaporiser for vaporising the at least one aerosol-forming substrate. In preferred embodiments, the vaporiser is substantially planar. The vaporiser may be any suitable device for vaporising the aerosol-forming substrate. For example, the vaporiser may be a piezoelectric or ultrasonic device, or a non-electric heater, such as a chemical heater. Preferably, the vaporiser comprises an electric heater including at least one heating element configured to heat the aerosol-forming substrate. In certain preferred embodiments, the cartridge comprises an electric heater including at least one heating element arranged to heat the at least one aerosol-forming substrate, wherein a contact surface between the electric heater and one or both of the base layer and the at least one aerosol-forming substrate is substantially planar and substantially parallel to the contact surface between the base layer and the at least one aerosol-forming substrate. This simplifies the manufacture of the cartridge by removing the need for any more complex assembly operations, such as rotational or multi-translational movements of the cartridge or its components. Preferably, the electric heater is substantially flat.

In any of the embodiments described above, the aerosol-forming cartridge may be a heated smoking article, which is a smoking article comprising an aerosol-forming substrate that is intended to be heated rather than combusted in order to release volatile compounds that can form an aerosol.

The cartridge may have any suitable outer shape. The cartridge may be an elongate aerosol-forming cartridge having a downstream end, through which aerosol exits the aerosol-generating article and is delivered to a user, and an opposed upstream end. In such embodiments components, or portions of components, of the aerosol-forming substrate may be described as being upstream or downstream of one another based on their relative positions between the proximal or downstream end and the distal or upstream end. Preferably, the cartridge is substantially flat. In certain embodiments, the cartridge is substantially flat and has a rectangular cross-section.

The cartridge may have any suitable size. Preferably, the cartridge has suitable dimensions for use with a handheld aerosol-generating system. In certain embodiments, the cartridge has length of from about 5 mm to about 200 mm, preferably from about 10 mm to about 100 mm, more preferably from about 20 mm to about 35 mm. In certain embodiments, the cartridge has width of from about 5 mm to about 12 mm, preferably from about 7 mm to about 10 mm. In certain embodiments, the cartridge has a height of from about 2 mm to about 10 mm, preferably form about 5 mm to about 8 mm.

In use, the cartridge may be connected to a separate mouthpiece portion by which a user can draw a flow of air through or adjacent to the cartridge by sucking on a downstream end of the mouthpiece portion. For example, the mouthpiece portion may be provided as part of an aerosol-generating device with which the cartridge is combined to form an aerosol-generating system. In such embodiments, the cartridge may comprise a flange for attaching a detachable mouthpiece portion. In certain preferred embodiments, the cartridge further comprises an integral mouthpiece portion. In such embodiments, preferably, the cartridge is arranged such that the resistance to draw at a downstream end of the mouthpiece portion is from about 50 mmWG to about 130 mmWG, preferably from about 80 mmWG to about 120 mmWG, more preferably from about 90 mmWG to about 110 mmWG, most preferably from about 95 mmWG to about 105 mmWG. As used herein, the term "resistance to draw" refers the pressure required to force air through the full length of the object under test at the rate of 17.5 ml/sec at 22 degrees Celsius and 101 kPa (760 Torr), is typically expressed in units of millimetres water gauge (mmWG) and is measured in accordance with ISO 6565: 2011.

The cartridge may comprise electric circuitry and electrical contacts connected to the electric circuitry for connection to corresponding electrical contacts on an aerosol-generating device with which the cartridge is intended for use.

The electrical contacts may comprise power contacts for supplying power to the cartridge as well as data contacts for transferring data to or from the cartridge, or both to and from the cartridge.

The electrical contacts may have any suitable form. The electrical contacts may be substantially flat. Advantageously, substantially flat electrical contacts have been found to be more reliable for establishing an electrical connection and are easier to manufacture. Preferably, the electrical contacts comprise part of a standardised electrical connection, including, but not limited to, USB-A, USB-B, USB-mini, USB-micro, SD, miniSD, or microSD type connections. Preferably, the electrical contacts comprise the male part of a standardised electrical connection, including, but not limited to, USB-A, USB-B, USB-mini, USB-micro, SD, miniSD, or microSD type connections. As used herein, the term "standardised electrical connection" refers an electrical connection which is specified by an industrial standard.

The electrical contacts may be formed integrally with the electric circuitry. In certain preferred embodiments, the cartridge comprises an electric heater to which the electrical contacts are connected. In such embodiments, the electric heater may comprise an electrically insulating substrate foil on or in which the electrical contacts and one or more heating elements are disposed.

According to a further aspect of the invention, there is provided a pack of aerosol-forming cartridges for use in an electrically heated aerosol-generating system, the pack containing a plurality of aerosol-forming cartridges according to any of the embodiments described above.

According to a further aspect of the invention, there is provided a method of manufacturing an aerosol-forming cartridge according to any of the embodiments described above.

The invention will now be further described, by way of example only, with reference to the accompanying drawings in which:

FIG. 2A is a perspective view and FIG. 2B is an exploded view of the cartridge;

FIG. 3A is a perspective view and FIG. 3B is an exploded view of the cartridge.

Figure 1A:
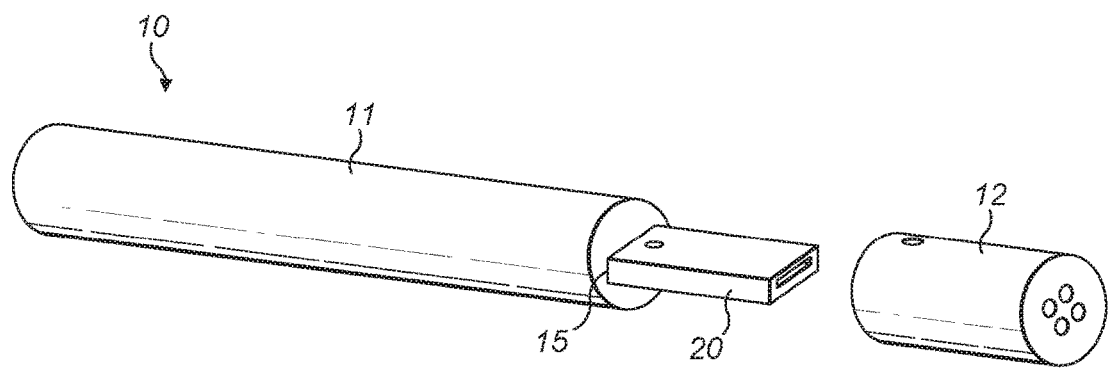
FIGS. 1A and 1B show a schematic illustration of an aerosol-generating system comprising an aerosol-forming cartridge in accordance with the present invention inserted into an electrically operated aerosol-generating device.
Figure 1B:
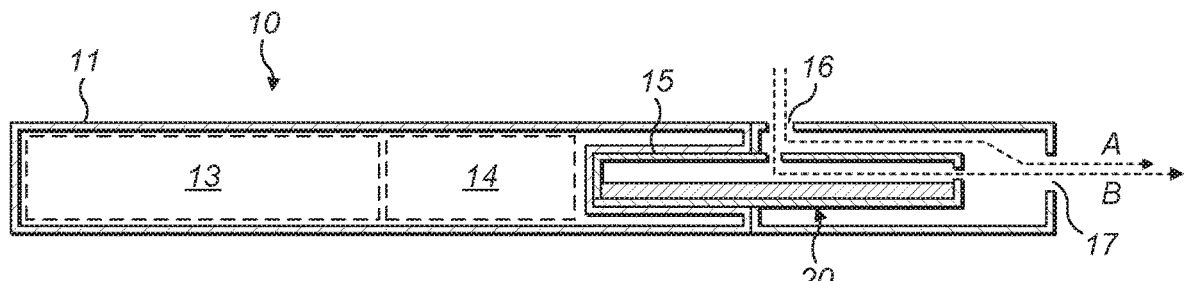

FIGS. 1A and 1B show an aerosol-generating device 10 and a separate, removable aerosol-forming cartridge 20, which together form an aerosol-generating system. The device 10 is portable and has a size comparable to a conventional cigar or cigarette. The device 10 comprises a main body 11 and a removable mouthpiece portion 12. The main body 12 contains a battery 13, such as a lithium iron phosphate battery, electric circuitry 14 and a slot-shaped cavity 15. The mouthpiece portion 12 fits over the cartridge and is connected to the main body 11 by a releasable connecting means (not shown). The mouthpiece portion 12 can be removed (as shown in FIG. 1) to allow for insertion and removal of cartridges and is connected to the main body 11 when the system is to be used to generate aerosol, as will be described. The mouthpiece portion 12 comprises an air inlet 16 and an air outlet 17, each of which may comprise one or more orifices. In use, a user sucks or puffs on the air outlet 17 to draw air from the air inlet 16, through the mouthpiece portion 12 to the air outlet 17, and thereafter into the mouth of the user. A flow of air drawn through the mouthpiece portion 12 may be drawn past the cartridge 20 (as shown by the arrows marked as "A" in FIG. 2), or also through one or more air flow channels in the cartridge 20 (as indicated by the arrows marked as "B" in FIG. 2). The cavity 15 has a rectangular cross-section and is sized to receive at least part of the cartridge 20 to removably connect the device 10 and the cartridge 20. As used herein, the term "removably connect" means that the device and the cartridge can be coupled and uncoupled from one another without significant damage to either.

Figure 2A:
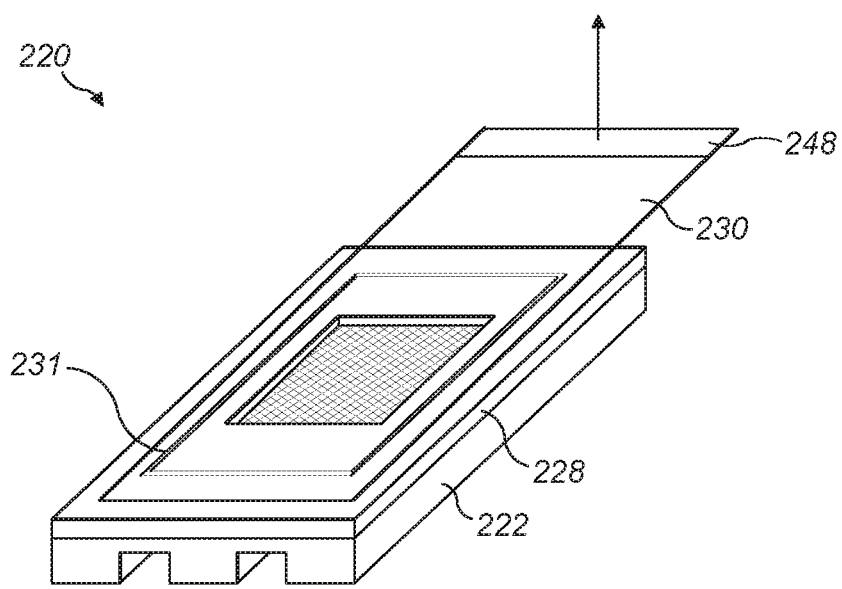
FIGS. 2A and 2B show a first embodiment of an aerosol-forming cartridge in accordance with the present invention, where
Figure 2B:
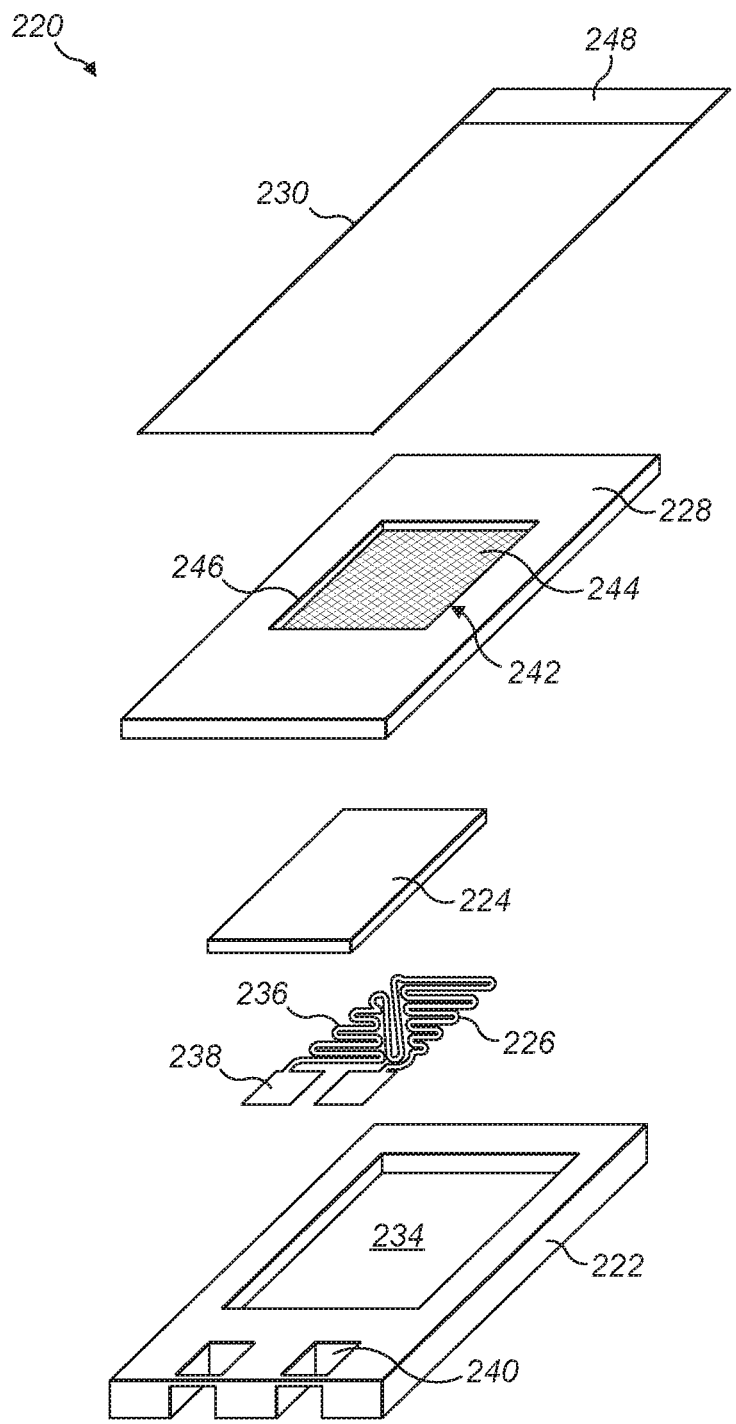

FIGS. 2A and 2B show a first embodiment of aerosol-forming cartridge 220. The cartridge 220 is substantially flat and has a rectangular cross-section, although it could have any other suitable flat shape. The cartridge comprises a base layer 222, an aerosol-forming substrate 224 arranged on the base layer 222, a heater 226 positioned between the aerosol-forming substrate 224 and the base layer 222, a cover layer 228 fixed to the base layer 222 and over the aerosol-forming substrate 224, and a protective foil 230 over the cover layer 228. The base layer 222, aerosol-forming substrate 224, heater 226, cover layer 228, and the protective foil 230 are all substantially flat and substantially parallel to each other. The contact surfaces between each of these components of the cartridge 220 are substantially planar and substantially parallel.

The base layer 222 has a cavity 234 defined on its top surface in which the heater 226 and the aerosol-forming substrate 224 are held. In this example, the aerosol-forming substrate 224 comprises a substantially flat rectangular block of tobacco cast leaf, although the aerosol-forming substrate may comprise any suitable material having volatile flavour compounds which are releasable from the aerosol-forming substrate 224 upon heating by the heater 226. For example, the aerosol-forming substrate could comprise any suitable tobacco-containing material having volatile flavour compounds which are releasable from the aerosol-forming substrate upon heating. Alternatively, or in addition, the aerosol-forming substrate could comprise any suitable nicotine-containing material, for example a nicotine-containing liquid absorbed in a porous carrier material, having volatile flavour compounds which are releasable from the aerosol-forming substrate upon heating.

The heater 226 comprises a heating element 236 connected to electrical contacts 238. In this example, the heating element 236 and electrical contacts 238 are integral and the heater 226 is formed by stamping a sheet of stainless steel. The base layer 222 has two contact apertures 240 at its distal end into which the electrical contacts 238 extend. The electric contacts 238 are accessible from outside of the cartridge through the contact apertures 240.

Advantageously, the cover layer 228 helps to keep the aerosol-forming substrate 224 in position on the base layer 222. The cover layer 228 has a permeable window 242 formed by a grid 244 extending across an opening 246 in the cover layer 228. In use, aerosol released by the aerosol-forming substrate 224 passes through the permeable window 242. The cover layer 228 is sized to fit over the cavity 234 in the base layer 222. In this example, the cover layer 228 extends laterally beyond the cavity 234 and has substantially the same width and length as the base layer 222 so the edges of the cover layer 228 and the base layer 222 are generally aligned.

The protective foil 230 is removably attached to the top of the cover layer 228 and over the permeable window 242 to seal the aerosol-forming substrate 224 within the cartridge 220. The protective foil 230 comprises a substantially gas impermeable sheet that is welded to the cover layer 228 but which can be easily peeled off. The sheet is welded to the cover layer 228, for example by ultrasonic welding, along a continuous sealing line 231 formed of two continuous weld lines arranged side by side. The protective foil 230 acts to prevent substantial loss of volatile compounds from the aerosol-forming substrate 224 prior to use of the cartridge 220. In this example, the protective foil 230 is formed from a flexible multilayer polymer sheet. A tab 248 is provided at the free end of the protective foil 230 to allow a user to grasp the protective foil 230 when peeling it off. The tab 248 is formed by an extension of the protective foil 230 and extends beyond the edge of the cover layer 228. It will be apparent to one of ordinary skill in the art that, although welding is described as the method to secure the removable protective foil 230 to the cover layer 228, other methods familiar to those in the art may also be used including, but not limited to, heat sealing or adhesive, provided the protective foil 230 may easily be removed by a consumer.

Prior to use of the cartridge, the protective foil 230 is removed by pulling the tab 248 in an upward direction to peel the protective foil 230 away from the cover layer 228. That is, the tab 248 is pulled in a direction having a component which is perpendicular to and away from the top surface of the cover layer 228, as indicated by the arrow in FIG. 2A. Once the protective foil 230 has been removed, the cartridge 220 is inserted into an aerosol-generating device, as shown in FIGS. 1A and 1B, so that the electrical contacts 238 of the cartridge 220 connect with corresponding electrical contacts in the cavity of the device. Electrical power is then provided by the device to the heater 226 of the cartridge to release aerosol from the aerosol-forming substrate 224. When a user sucks or puffs on the air outlet of the mouthpiece portion of the device, air is drawn through the mouthpiece and across the gas permeable window 242 in the cover layer 228 where it is mixed with the aerosol. The air and aerosol mixture is then drawn through the outlet of the mouthpiece portion and thereafter into the mouth of the user.

Once the aerosol-forming substrate 224 has been consumed, the cartridge is removed from the cavity of the device and replaced.

Figure 2C:
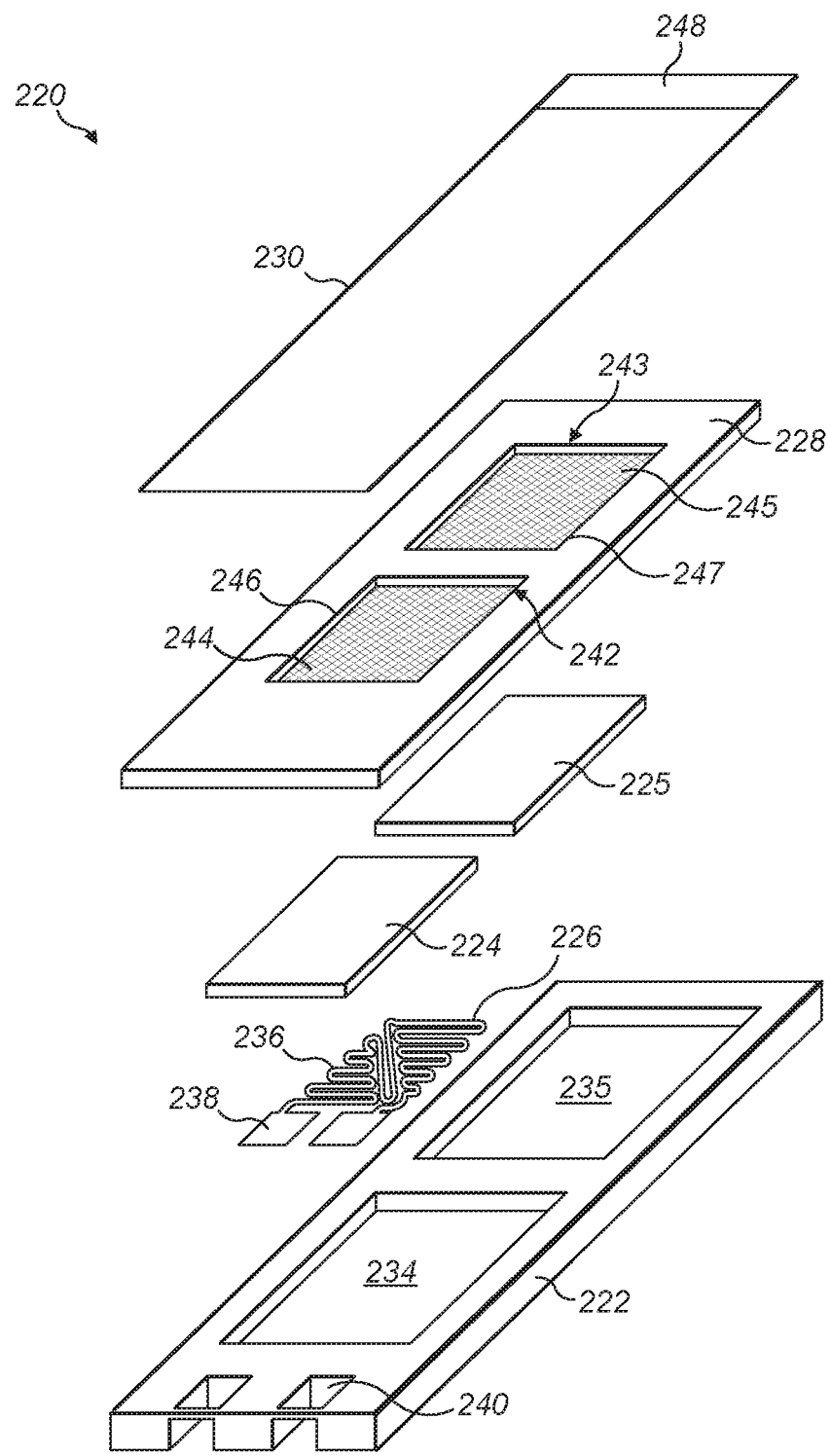
FIG. 2C shows an exploded view of a variation of the aerosol-forming cartridge of FIGS. 2A and 2B.

FIG. 2C shows an exploded view of a variation of the cartridge 220. In the variation shown in FIG. 2C, the cavity 234 is a first cavity and the base layer 222 defines a second cavity 235. The aerosol-forming substrate 224 is a first aerosol-forming substrate and the cartridge 220 comprises a second aerosol-forming substrate 225 held in the second cavity 235. The permeable window 242 is a first permeable window and the cover layer 228 defines a second permeable window 243 formed by a grid 245 extending across an opening 247 in the cover layer 228. In use, aerosol released by the second aerosol-forming substrate 225 passes through the second permeable window 243.

Figure 3A:
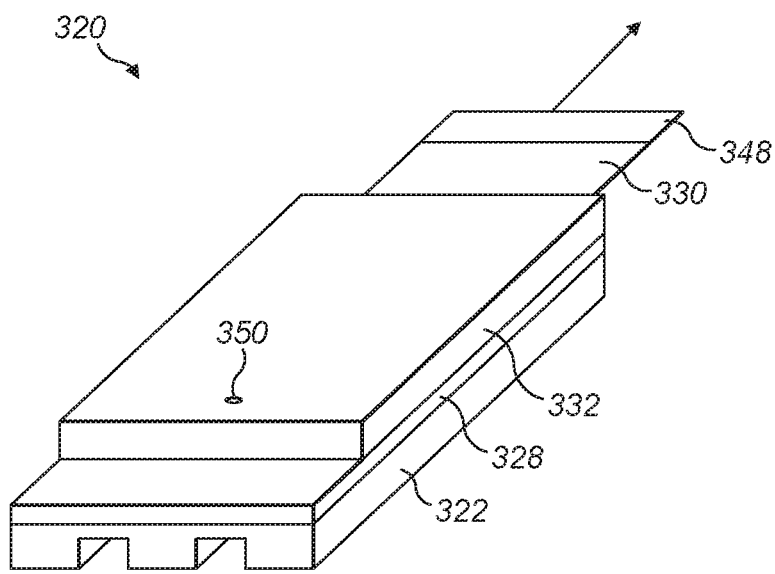
FIGS. 3A and 3B show a second embodiment of an aerosol-forming cartridge in accordance with the present invention, where
Figure 3B:
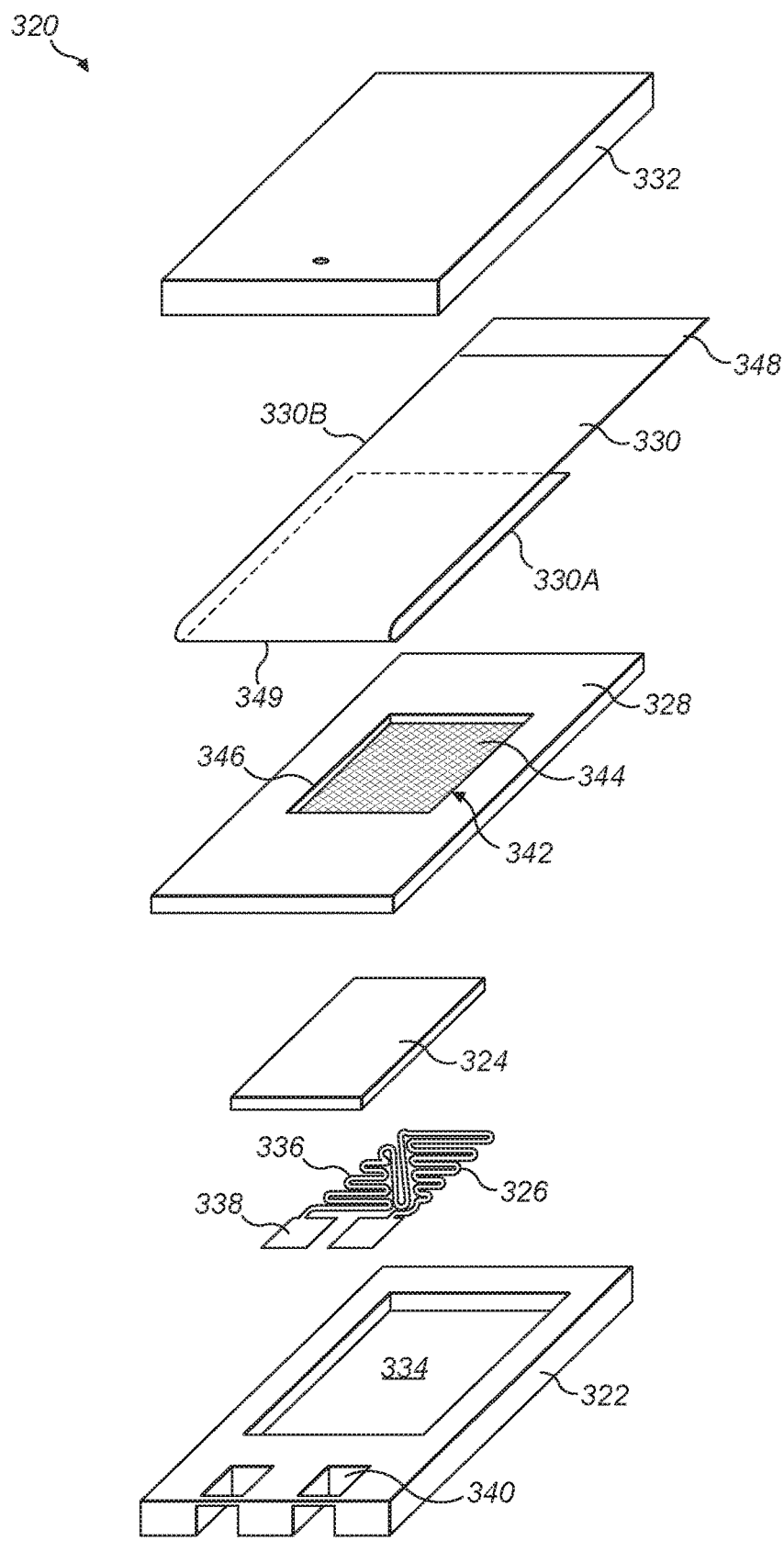

FIGS. 3A and 3B show a second embodiment of aerosol-forming cartridge 320. The cartridge 320 is substantially flat and has a rectangular cross-section, although it could have any other suitable flat shape. The cartridge comprises a base layer 322, an aerosol-forming substrate 324 arranged on the base layer 322, a heater 326 positioned between the aerosol-forming substrate 324 and the base layer 322, a cover layer 328 fixed to the base layer 322 and over the aerosol-forming substrate 324, a protective foil 330 over the cover layer 328 and a top cover 332 fixed to the cover layer 328 and over the cover layer 328 and the protective foil 330. The base layer 322, aerosol-forming substrate 324, heater 326, cover layer 328, protective foil 330 and top cover 332 are all substantially flat and substantially parallel to each other. The contact surfaces between each of these components of the cartridge 320 are substantially planar and substantially parallel.

The base layer 322 has a cavity 334 defined on its top surface in which the heater 326 and the aerosol-forming substrate 324 are held. In this example, the aerosol-forming substrate 324 comprises a substantially flat rectangular block of tobacco cast leaf, although the aerosol-forming substrate may comprise any suitable material having volatile flavour compounds which are releasable from the aerosol-forming substrate 324 upon heating by the heater 326. For example, the aerosol-forming substrate could comprise any suitable tobacco-containing material having volatile flavour compounds which are releasable from the aerosol-forming substrate upon heating. Alternatively, or in addition, the aerosol-forming substrate could comprise any suitable nicotine-containing material, for example a liquid nicotine source absorbed in a porous carrier material, having volatile flavour compounds which are releasable from the aerosol-forming substrate upon heating.

The heater 326 comprises a heating element 336 connected to electrical contacts 338. In this example, the heating element 336 and electrical contacts 338 are integral and the heater 326 is formed by stamping a sheet of stainless steel. The base layer 322 has two contact apertures 340 at its distal end into which the electrical contacts 338 extend. The electric contacts 338 are accessible from outside of the cartridge through the contact apertures 340.

Advantageously, the cover layer 328 helps to keep the aerosol-forming substrate 324 in position on the base layer 322. The cover layer 328 has a permeable window 342 formed by a grid 344 extending across an opening 346 in the cover layer 328. In use, aerosol released by the aerosol-forming substrate 324 passes through the permeable window 342. The cover layer 328 is sized to fit over the cavity 334 in the base layer 322. In this example, the cover layer 328 extends laterally beyond the cavity 334 and has substantially the same width and length as the base layer 322 so the edges of the cover layer 328 and the base layer 322 are generally aligned.

The protective foil 330 is removably attached to the top of the cover layer 328 and over the permeable window 342 to seal the aerosol-forming substrate 324 within the cartridge 320. The protective foil 330 comprises a substantially liquid impermeable sheet that is welded to the cover layer 328 but which can be easily peeled off. The sheet is welded to the cover layer 328, for example by ultrasonic welding, along a continuous sealing line (not shown) formed of two continuous weld lines arranged side by side. The protective foil 330 acts to prevent substantial loss of volatile compounds from the aerosol-forming substrate 324 prior to use of the cartridge 320. In this example, the protective foil 330 is formed from a flexible multilayer polymer sheet. A tab 348 is provided at the free end of the protective foil 330 to allow a user to grasp the protective foil 330 when peeling it off. The tab 348 is formed by an extension of the protective foil 330 and extends beyond the edge of the cover layer 328. In this example, the top cover 332 is fixed over the protective foil 330 so prevents the protective foil 330 from being removed by peeling the tab 348 upwards. To facilitate removal, the protective foil 330 is folded over itself at a fold line 349 such that the protective foil 330 divided into a first portion 330A, which is attached to the cover layer 328 by the continuous sealing line, and a second portion 330B, which extends longitudinally from the fold line 349 to the tab 348. The section portion 330B lies flat against the first portion 330A so that the first and second portions 330A, 330B are substantially co-planar. With this arrangement, the protective foil 330 can be removed by pulling the tab 348 longitudinally, rather than upwardly, to peel the first portion 330A away from the cover layer 328 at the fold line 349.

It will be apparent to one of ordinary skill in the art that, although welding is described as the method to secure the removable protective foil 330 to the cover layer 328, other methods familiar to those in the art may also be used including, but not limited to, heat sealing or adhesive, provided the protective foil 330 may easily be removed by a consumer.

The top cover 332 is hollow and includes an air inlet 350 towards its distal end and an air outlet (not shown) at its proximal end. The air inlet 350 and the air outlet are connected by an air flow channel (not shown) which is defined beneath the top cover 332. The air flow channel is separated from the aerosol-forming substrate 324 by the protective foil 330.

Prior to use of the cartridge 320, the protective foil 330 is removed by pulling the tab 348 longitudinally to peel the first portion 330A away from the cover layer 328. That is, the tab 348 is pulled in a direction having a component which is parallel to the plane of the protective foil 330 and perpendicular to the fold line 349, as indicated by the arrow in FIG. 3A. Once the protective foil 330 has been removed, the aerosol-forming substrate 324 and the air flow channel are connected via the permeable window 342 in the cover layer 328. The cartridge 320 is then inserted into an aerosol-generating device, as shown in FIGS. 1A and 1B, so that the electrical contacts 338 connect with the corresponding electrical contacts in the cavity of the device. When electrical power is provided by the device to the heater 326 of the cartridge, aerosol is released from the aerosol-forming substrate 324. When a user sucks or puffs on the mouthpiece portion of the device, air is drawn from the air inlets in the mouthpiece portion, into the air inlet 350 of the top cover and through the air flow channel in the top cover, where it is mixed with aerosol passing through the permeable window 342. The air and aerosol mixture is then drawn through the air outlet of the cartridge to the outlet of the mouthpiece portion and thereafter into the mouth of the user.

Once the aerosol-forming substrate 324 has been consumed, the cartridge is removed from the cavity of the device and replaced.

The exemplary embodiments described above illustrate but are not limiting. In view of the above discussed exemplary embodiments, other embodiments consistent with the above exemplary embodiments will now be apparent to one of ordinary skill in the art.

The invention claimed is:

1. An aerosol-forming cartridge for an electrically operated aerosol-generating system, the aerosol-forming cartridge comprising:
   a base layer comprising at least one cavity;
   at least one aerosol-forming substrate held in the at least one cavity, the aerosol-forming substrate comprising a tobacco-containing material with volatile tobacco flavour compounds, which are releasable from the aerosol-forming substrate upon heating, or a nicotine-containing liquid substrate with volatile nicotine compounds, which are releasable from the aerosol-forming substrate upon heating;

a vaporiser comprising an electric heater including at least one heating element configured to heat the aerosol-forming substrate; and a protective foil removably attached to the base layer and arranged to substantially hermetically seal the at least one aerosol-forming substrate within the at least one cavity, wherein the base layer and the at least one aerosol-forming substrate are in contact at a substantially planar first contact surface, and the base layer and the protective foil are in contact at a substantially planar second contact surface, and wherein the first and second contact surfaces are substantially parallel.

2. The aerosol-forming cartridge of claim 1, further comprising a cover layer fixed to the base layer and over the at least one aerosol-forming substrate to retain the at least one aerosol-forming substrate in the at least one cavity, the cover layer comprising at least one gas-permeable window.

3. The aerosol-forming cartridge of claim 2, wherein the protective foil is substantially planar and is arranged to substantially hermetically seal the aerosol-forming substrate within the at least one cavity by closing the at least one gas-permeable window.

4. The aerosol-forming cartridge of claim 3,
wherein an area of the at least one gas-permeable window is less than an area of the at least one cavity, and
wherein a remainder of the cover layer is substantially gas-impermeable.

5. The aerosol-forming cartridge of claim 1, wherein at least one of the base layer, the protective foil, and the at least one aerosol-forming substrate is substantially flat.

6. The aerosol-forming cartridge of claim 1, wherein the protective foil is removably attached to the base layer by ultrasonic welding along a continuous sealing line.

7. The aerosol-forming cartridge of claim 6, wherein the continuous sealing line comprises first and second continuous weld lines arranged side by side.

8. The aerosol-forming cartridge of claim 1, wherein the protective foil is removably attached to the base layer by an adhesive.

9. The aerosol-forming cartridge of claim 1, wherein the protective foil is formed from a flexible film comprising a polymer film, a metallised film, a metallised paper film, a laminated metal foil, or any combination thereof.

10. The aerosol-forming cartridge of claim 1, wherein the protective foil comprises a first portion that is removably attached to the base layer and a second portion that is attached to the first portion, the second portion extending beyond the base layer to form a tab by which a user can remove the first portion from the base layer.

11. The aerosol-forming cartridge of claim 10, wherein the second portion is folded over the first portion at a fold line such that the first portion and the second portion are substantially coplanar.

12. The aerosol-forming cartridge of claim 1,
wherein the at least one aerosol-forming substrate comprises first and second aerosol-forming substrates and the base layer comprises first and second cavities in which the first and second aerosol-forming substrates are stored separately, and
wherein the protective foil is configured for removal in stages to selectively open the first and second cavities independently.

13. The aerosol-forming cartridge of claim 1, wherein the aerosol-forming substrate comprises a flavour carrier with volatile flavour compounds that are releasable from the aerosol-forming substrate upon heating.

14. A pack of aerosol-forming cartridges for an electrically heated aerosol-generating system, the pack containing a plurality of aerosol-forming cartridges each comprising:

a base layer comprising at least one cavity;

at least one aerosol-forming substrate held in the at least one cavity, the aerosol-forming substrate comprising a tobacco-containing material with volatile tobacco flavour compounds, which are releasable from the aerosol-forming substrate upon heating, or a nicotine-containing liquid substrate with volatile nicotine compounds, which are releasable from the aerosol-forming substrate upon heating;

a vaporiser comprising an electric heater including at least one heating element configured to heat the aerosol-forming substrate; and a protective foil removably attached to the base layer and arranged to substantially hermetically seal the at least one aerosol-forming substrate within the at least one cavity, wherein the base layer and the at least one aerosol-forming substrate are in contact at a substantially planar first contact surface, and the base layer and the protective foil are in contact at a substantially planar second contact surface, and wherein the first and second contact surfaces are substantially parallel.

* * * * *